United States Patent
Heidemann et al.

(10) Patent No.: US 8,779,205 B2
(45) Date of Patent: Jul. 15, 2014

(54) METHOD FOR PRE-TREATING HYDROAMINATION CATALYSTS

(75) Inventors: Thomas Heidemann, Viernheim (DE); Marcus Sigl, Mannheim (DE)

(73) Assignee: BASF SE, Ludwigshafen (DE)

( * ) Notice: Subject to any disclaimer, the term of this patent is extended or adjusted under 35 U.S.C. 154(b) by 774 days.

(21) Appl. No.: 12/601,653

(22) PCT Filed: Apr. 7, 2009

(86) PCT No.: PCT/EP2009/054124
§ 371 (c)(1),
(2), (4) Date: Nov. 24, 2009

(87) PCT Pub. No.: WO2009/124924
PCT Pub. Date: Oct. 15, 2009

(65) Prior Publication Data
US 2010/0174117 A1    Jul. 8, 2010

(30) Foreign Application Priority Data

Apr. 9, 2008 (EP) ..................................... 08154266

(51) Int. Cl.
*C07C 209/00* (2006.01)

(52) U.S. Cl.
USPC ....................................................... 564/485

(58) Field of Classification Search
None
See application file for complete search history.

(56) References Cited

U.S. PATENT DOCUMENTS

| | | |
|---|---|---|
| 4,375,002 A | 2/1983 | Peterson et al. |
| 4,536,602 A | 8/1985 | Deeba |
| 4,929,758 A | 5/1990 | Taglieber et al. |
| 4,929,759 A | 5/1990 | Taglieber et al. |
| 5,648,546 A | 7/1997 | Bergfeld et al. |
| 5,763,668 A | 6/1998 | Dingerdissen et al. |
| 5,786,510 A | 7/1998 | Eller et al. |
| 5,817,871 A | 10/1998 | Dingerdissen et al. |
| 6,143,934 A | 11/2000 | Dingerdissen et al. |
| 6,350,914 B1 | 2/2002 | Eller et al. |
| 6,576,796 B1 | 6/2003 | Funke et al. |
| 7,074,964 B2 * | 7/2006 | Sigl et al. ..................... 564/485 |
| 7,642,383 B2 * | 1/2010 | Sigl et al. ..................... 564/485 |
| 2008/0319230 A1 | 12/2008 | Sigl et al. |

FOREIGN PATENT DOCUMENTS

| | | |
|---|---|---|
| CA | 2092964 A1 | 6/1994 |
| DE | 4206992 A1 | 9/1993 |
| DE | 4431093 A1 | 3/1996 |
| DE | 19530177 A1 | 2/1997 |
| DE | 19601409 A1 | 7/1997 |
| DE | 10313853 A1 | 10/2004 |
| DE | 102005051044 A1 | 4/2007 |
| EP | 0101921 A1 | 3/1984 |
| EP | 0132736 A2 | 2/1985 |
| EP | 0133938 A2 | 3/1985 |
| EP | 0305564 A1 | 3/1989 |
| EP | 0431451 A2 | 6/1991 |
| EP | 0752409 A2 | 1/1997 |
| EP | 0822179 A2 | 2/1998 |
| EP | 1 462 165 A1 | 9/2004 |
| WO | WO-97/07088 A1 | 2/1997 |
| WO | WO-02/00597 A2 | 1/2002 |
| WO | WO2007048753 * 5/2007 ............ C07C 209/60 |

OTHER PUBLICATIONS

Hara, H. Chemistry Letters, pp. 713-716, 1988.*
Socrates, G. J. Chem. Education, 1969, 46 (11), p. 710.*
U.S. Appl. No. 13/265,457, filed Oct. 20, 2011, Heidemann et al.
Bibby, D.M. et al, "Coke formation in high-silica zeolites" Applied Catalysis A: General, 1992, pp. 1-34, vol. 93, Elsevier Science Publishers B.V.
Van Den Berg, J.P. et al., "Low-Temperature Oligomerization of Small Olefins on Zeolite H-ZSM-5. An investigation with High-Resolution Solid-State $^{13}$C-NMR" Journal of Catalysis, 1983, pp. 130-138, vol. 80, Academic Press.
Ping et al., "Domertic Market and Progress in Production Technology of Tert-butylamine", Liaoning Chemical Industry, Feb. 2001, vol. 30, No. 2, pp. 64, 65, 74.

* cited by examiner

*Primary Examiner* — Clinton Brooks
(74) *Attorney, Agent, or Firm* — Drinker Biddle & Reath LLP

(57) ABSTRACT

The present invention relates to a process for the pretreatment of hydroamination catalysts, wherein the hydroamination catalyst is brought into contact with an ammonia-comprising mixture before the reaction of olefins with ammonia, a primary or secondary amine, with the ammonia-comprising mixture comprising less than 40% by weight of olefin The invention further relates to a process for preparing alkylamines by reaction of olefins with ammonia, primary or secondary amines over a hydroamination catalyst, wherein the hydroamination catalyst is pretreated according to the invention before the reaction of the olefins by bringing the hydroamination catalyst into contact with an ammonia-comprising mixture comprising less than 40% by weight of olefin.

16 Claims, No Drawings

METHOD FOR PRE-TREATING HYDROAMINATION CATALYSTS

CROSS-REFERENCE TO RELATED APPLICATIONS

This application is a national stage application (under 35 U.S.C. §371) of PCT/EP2009/054124, filed Apr. 7 2009, which claims benefit of European application 08154266.4, filed Apr. 9, 2008, the contents of which are incorporated herein by reference.

FIELD OF THE INVENTION

The present invention relates to a process for the pretreatment of hydroamination catalysts. The invention further relates to a process for preparing alkylamines by reaction of olefins with ammonia, primary or secondary amities over a hydroamination catalyst which is brought into contact with an ammonia-comprising mixture before the reaction of the olefins with ammonia, with the ammonia-comprising mixture comprising less than 40% by weight of olefin.

BACKGROUND OF THE INVENTION

It is known from EP-A-0133938 that alumino-zeolite catalysts used in the hydroamination reaction deactivate quickly since these catalysts promote polymerization or oligomerization of the olefins used on the catalyst and subsequent carbonization of these polymeric or oligomeric residues on the catalysts. EP-A-0133938 teaches that deactivation of the catalysts can be reduced when ammonia, primary or secondary amines are reacted with olefins in the presence of borosilicate or borogermanate zeolite catalysts of the pentasil type, the amine obtained is separated off and the unreacted starting materials are recirculated. Furthermore, it is disclosed that deactivated catalysts can be regenerated by passing air or an air/nitrogen mixture over the catalyst at from 400 to 550° C.

WO-A-97/07088 discloses the hydroamination of olefins in the presence of boron-BETA-zeolite catalysts. This application mentions various factors which can influence the deactivation of catalysts. Thus, it is taught that monoolefins have a less pronounced tendency to polymerize than do diolefins or polyolefins. Higher temperatures are said to promote the polymerization and the cracking reaction of the olefins used. The activity of the catalysts can, according to the disclosure, be restored by regeneration in an oxygen-comprising gas at elevated temperatures.

The prior art teaches that the polymerization of the olefins used in the hydroamination reaction and the carbonization resulting therefrom can lead to deactivation of the catalysts used. Factors such as the type and nature of the catalyst, the reaction temperature, the type of olefin can influence the rate and the degree of deactivation. The activity is usually restored by regeneration of the catalysts by passing an oxygen-comprising gas over the catalyst at a temperature in the range from 400 to 550° C.

DE-A-10313853 teaches that the activity of calcined, zeolytic catalysts can be increased when the calcined catalyst is treated at temperatures in the range from 100 to 550° C. in an oxygen-comprising gas stream a maximum of 24 hours before commencement of the reaction. According to the disclosure, an increase in the activity occurs regardless of whether the catalyst is used for the first time in the hydroamination or whether a previously regenerated catalyst is used.

DE-A-102005051044 discloses that the hydroamination is generally carried out in an adiabatically operated reaction unit.

When starting up zeolytic catalysts, i.e. when the catalyst is first brought into contact with the feed mixture of olefin and ammonia or amine, a temperature increase is generally observed since the heat produced during start-up can be removed only with great difficulty in the case of industrial, adiabatically operated reactors. This temperature increase generally promotes the oligomerization of the olefins used. Since the oligomerization is generally an exothermic reaction, the heat liberated in this reaction additionally accelerates the temperature rise. The high temperatures occurring in the start-up process generally lead to damage to the catalyst caused by deposition of the olefin oligomers on the catalyst surface and in the pores or even to a change in the zeolite structure itself.

BRIEF SUMMARY OF THE INVENTION

It was therefore an object of the present invention to provide a hydroamination process in which the thermal damage to the hydroamination catalysts during start-up of the catalyst is reduced. A hydroamination process which has long periods of operation and makes it possible to obtain hydroamination product in a very high yield and selectivity should be provided. The operating life of the catalyst before regeneration may be required should be increased. A further object of the present invention was to develop a process for the pretreatment of a hydroamination catalyst, which process leads to reduced thermal damage to the catalysts used so that the activity of the catalysts is retained for a long time.

According to the invention, the object is achieved by a process for the pretreatment of hydroamination catalysts, wherein the hydroamination catalyst is brought into contact with an ammonia-comprising mixture before the reaction of olefins with ammonia, a primary or secondary amine, with the ammonia-comprising mixture comprising less than 40% by weight of olefin.

In addition, the object is achieved by a process for preparing alkylamines by reaction of olefins with ammonia, primary or secondary amines over a hydroamination catalyst, wherein the hydroamination catalyst is brought into contact with an ammonia-comprising mixture before the reaction of the olefins with ammonia, primary or secondary amines, with the ammonia-comprising mixture comprising less than 40% by weight of olefin.

DETAILED DESCRIPTION OF THE PREFERRED EMBODIMENTS

According to the invention, hydroamination catalysts are brought into contact with an ammonia-comprising mixture before the reaction of olefins with ammonia, a primary or secondary amine, with the ammonia-comprising mixture comprising less than 40% by weight of olefin.

The ammonia-comprising mixture preferably comprises commercial ammonia. In general, commercial ammonia having an ammonia content of greater than 95% by weight, preferably greater than 98% by weight, particularly preferably greater than 99% by weight, in particular greater than 99.5% by weight, is used.

In a further preferred embodiment, the hydroamination catalysts are brought into contact with an ammonia-comprising mixture comprising olefin in addition to ammonia. The olefin used in addition to ammonia is preferably the olefin used in the subsequent hydroamination reaction.

According to the invention, the ammonia-comprising mixture comprises less than 40% by weight of olefin. The ammonia-comprising mixture particularly preferably comprises less than 10% by weight, particularly preferably less than 5% by weight, very particularly preferably less than 1% by weight, of olefin.

In general, the ammonia-comprising mixture comprises no further constituents in addition to ammonia and, if appropriate, an olefin. However, it is possible for the ammonia-comprising mixture to comprise further constituents, for example water or another primary or secondary amine. In general, however, the proportion of further constituents is preferably less than 5% by weight, particularly preferably less than 2% by weight and very particularly preferably less than 1% by weight.

The hydroamination catalyst is preferably brought into contact with the ammonia-comprising mixture at a temperature of from 0 to 50° C., preferably from 10 to 30° C.

The preferred pressure at which the hydroamination catalyst is brought into contact with the ammonia-comprising mixture is in the range from 0.1 to 50 bar abs., preferably in the range from 0.5 to 20 bar abs. and particularly preferably in the range from 1 to 10 bar abs.

The ammonia-comprising mixture can be brought in gaseous or liquid form into contact with the hydroamination catalyst.

The hydroamination catalyst is usually brought into contact with the ammonia-comprising mixture by filling the reactor comprising the catalyst with liquid ammonia-comprising mixture. Preference is given to wetting all the hydroamination catalyst present in the reactor with liquid ammonia-comprising mixture.

The liquid ammonia-comprising mixture can also be passed continuously over the hydroamination catalyst. The space velocity over the catalyst is generally in the range (0.1 to 20 kg of ammonia-comprising mixture)/(kg of catalyst)/minute, preferably (0.5 to 10 kg of ammonia-comprising mixture)/(kg of catalyst)/minute.

The ammonia-comprising mixture can also be passed in gaseous form over the hydroamination catalyst. The space velocity of the catalyst is generally in the range (0.1 to 20 l of ammonia-comprising mixture)/(kg of catalyst)/minute, preferably (0.5 to 10 l of ammonia-comprising mixture)/(kg of catalyst)/minute.

The duration of the contacting of the hydroamination catalyst with the ammonia-comprising mixture is generally in the range from 5 minutes to 24 hours, preferably from 10 minutes to 12 hours and particularly preferably from 30 minutes to 6 hours.

The hydroamination catalyst can be brought into contact with the ammonia-comprising mixture outside the reactor in which the hydroamination is carried out.

However, the hydroamination catalyst is preferably brought into contact with the ammonia-comprising mixture in the reactor in which the subsequent hydroamination is carried out. This reactor is preferably a continuously operated reactor, for example a tube reactor or a fluidized-bed reactor.

In a preferred embodiment, the ammonia-comprising mixture is brought into contact with the hydroamination catalyst together with inert gases, for example nitrogen, argon, helium or mixtures thereof. The introduction of inert gases into the ammonia-comprising mixture has the advantage that the inert gases can remove heat from the catalyst.

The flow of inert gases over the hydroamination catalyst is usually in the range from (1 l of inert gas)/(kg of catalyst)/minute to (1000 l of inert gas)/(kg of catalyst)/minute, preferably from (5 l of inert gas)/(kg of catalyst)/minute to (100 l of inert gas)/(kg of catalyst)/minute, particularly preferably from (10 l of inert gas)/(kg of catalyst)/minute to (50 l of inert gas)/(kg of catalyst)/minute.

In a particularly preferred embodiment, the hydroamination catalyst is thermally treated in accordance with the teachings of DE-A-10313853 before being brought into contact with the ammonia-comprising mixture. The thermal treatment can preferably be carried out at temperatures in the range from 100 to 550° C. in a gas stream composed of air, nitrogen, other inert gases or mixtures thereof.

In a preferred embodiment, the hydroamination catalysts used in the process of the invention have not yet been used in a hydroamination reaction, i.e. they are catalysts over which no reaction of olefins with ammonia, primary or secondary amines has yet been carried out.

However, the process can also be carried out using hydroamination catalysts which have already been used in a hydroamination reaction and which have been regenerated in an oxygen-comprising gas at elevated temperatures, preferably at temperatures of from 400 to 550° C., in a customary fashion subsequent to the hydroamination reaction.

After the hydroamination catalyst has been brought into contact with the ammonia-comprising mixture, olefins can be reacted with ammonia, primary or secondary amines to form alkylamines over the hydroamination catalyst.

The present invention accordingly provides a process for preparing alkylamines by reaction of olefins with ammonia, primary or secondary amines over a hydroamination catalyst, characterized in that the hydroamination catalyst is pretreated according to the invention by bringing the hydroamination catalyst into contact with an ammonia-comprising mixture before the reaction of olefins with ammonia, primary or secondary amines, with the ammonia-comprising mixture comprising less than 40% by weight of olefin.

As hydroamination catalysts, preference is given to using calcined zeolytic catalysts.

In zeolytic hydroamination catalysts, the active composition is made up of zeolites. Zeolytic hydroamination catalysts usually further comprise binders which are necessary for producing shaped catalyst bodies. In the production of the shaped catalyst bodies from appropriate molding compositions, drying is usually followed by calcination in order to obtain the final catalyst.

The step which concludes the shaping of the shaped catalyst bodies is calcination. Here, a temperature of above 400° C. is generally required to harden the binder material. The maximum temperature is restricted by the stability of the zeolite which looses its crystallinity at temperatures above 550° C. The calcination is carried out industrially in a rotating tube at a temperature in the range from 400 to 560° C. and a residence time of from 2 to 4 hours. In the laboratory, it is usually carried out in a furnace at a temperature of from 480 to 520° C. and for a time of from 2 to 32 hours.

Hydroamination catalysts for the hydroamination of olefins by means of ammonia and/or a primary or secondary amine are generally zeolites, in particular faujasites such as X-, Y- and USY-zeolite, erionite, chabazite, mordenite, offretite, clinoptiolite, pentasils such as ZSM-5 and ZBM-10, ZSM-11, ZSM-12, MCM-22, MCM-41, MCM-48, MCM-49, MCM-56, EMT, SSZ-26, SSZ-33, SSZ-37, CIT-1, PSH-3, NU-85, beta and also the boron-comprising forms, for example ZBM-11, H-boron-ZSM-5, H-boron-beta, H-boron-ZSM-11 and also the gallium- or titanium-comprising forms. They have a large number of catalytically active sites, combined with a large surface area.

The zeolites described differ in terms of type and in the manner of after-treatment after their preparation (for example thermal treatment, dealumination, acid treatment, metal ion exchange, etc.).

Examples of zeolites may be found in U.S. Pat. Nos. 4,375, 002, 4,536,602, EP-A 305 564, EP-A 101 921 and DE-A 42 06 992.

The zeolites known from EP-A 133 938, EP-A 431 451 and EP-A 132 736, which are boron silicate, gallium silicate, aluminosilicate and iron silicate zeolites which may, if appropriate, be doped as described with alkali, alkaline earth and transition metals, can also be used in the process of the invention.

Furthermore, it is possible to use, for example, the beta-zeolites known from CA-A 2 092 964, which are defined as crystallized aluminosilicates having a particular composition and a pore size of more than 5 Å.

Preference is given to using metal- or halogen-modified beta-zeolites, as described, for example, in DE-A 195 30 177.

Very particular preference is also given to zeolite catalysts of the pentasil type having a molar $SiO_2/Al_2O_3$ ratio of greater than/equal to 10, as disclosed in EP-A 132 736.

Aluminum phosphates and silicoaluminophosphates include the crystalline systems having zeolite structures or zeolite-like structures, for example SAPO-37, $AlPO_4$-5, SAPO-5, as described in DE-A 196 01 409, but also amorphous systems as are described, for example, in DE-A 44 31 093. They generally have the formula $Al_2O_3*P_2O_5*xSiO_2$.

The hydroamination catalysts can be used in the form of powder or preferably in the form of shaped bodies such as extrudates, pellets or crushed material. For carrying out shaping, it is possible to add from 2 to 60% by weight (based on the composition to be shaped) of binders. Suitable binders are various aluminum oxides, preferably boehmite, amorphous aluminosilicates having a molar $SiO_2/Al_2O_3$ ratio of from 25:75 to 95:5, silicon dioxide, preferably finely divided $SiO_2$, for example silica sols, mixtures of finely divided $SiO_2$ and finely divided $Al_2O_3$, finely divided $TiO_2$ and clays.

In general, the hydroamination catalysts are used in the H form. However, various modifications can be carried out on the hydroamination catalysts to increase the selectivity, the operating life and the number of possible catalyst regenerations.

Modification of the hydroamination catalysts comprises ion-exchanging or doping the unshaped hydroamination catalysts with alkali metals such as Na and K, alkaline earth metals such as Ca, Mg, heavy metals such as Tl, transition metals such as Mn, Fe, Mo, Cu, Zn, Cr, noble metals and/or rare earth metals such as La, Ce or Y.

An advantageous catalyst treatment comprises placing the shaped hydroamination catalysts in a flow tube and passing, for example, a halide, an acetate, an oxalate, a citrate or a nitrate of the above-described metals in dissolved form over the catalysts at from 20 to 100° C. Such an ion exchange can, for example, be carried out on the hydrogen, ammonium or alkali metal form of the hydroamination catalysts.

Another possible way of applying a metal to the hydroamination catalysts is to impregnate the zeolytic material with, for example, a halide, acetate, oxalate, citrate, nitrate or oxide of the above-described metals in aqueous or alcoholic solution.

Both an ion exchange and an impregnation can be followed by drying and, if desired, another calcination. In the case of metal-doped hydroamination catalysts, an after-treatment with hydrogen and/or with steam can be advantageous.

A further possible way of modifying the catalyst is to subject the heterogeneously catalytic material, shaped or unshaped, to a treatment with acids such as hydrochloric acid (HCl), hydrofluoric acid (HF), phosphoric acid ($H_3PO_4$), sulfuric acid ($H_2SO_4$), oxalic acid ($HO_2C—CO_2H$) or mixtures thereof.

A particular embodiment comprises treating the catalyst powder with hydrofluoric acid (from 0.001 to 2 molar, preferably from 0.05 to 0.5 molar) under reflux for from 1 to 3 hours before shaping. After filtration and washing, the catalyst powder is generally dried at from 100 to 160° C. and calcined at from 400 to 550° C.

A further particular embodiment comprises HCl treatment of the heterogeneous catalysts after they have been shaped with binders. Here, the heterogeneous catalyst is generally treated with a 3-25% strength, in particular a 12-20% strength, hydrochloric acid at temperatures of from 60 to 80° C. for from 1 to 3 hours, subsequently washed, dried at from 100 to 160° C. and calcined at from 400 to 550° C.

Another possible way of modifying the catalyst is exchange with ammonium salts, for example with $NH_4Cl$, or with monoamines, diamines or polyamines. Here, the heterogeneous catalyst which has been shaped with a binder is generally exchanged continuously with 10-25% strength, preferably about 20% strength, $NH_4Cl$ solution in a weight ratio of heterogeneous catalyst/ammonium chloride solution of 1:15 at from 60 to 80° C. for 2 hours and then dried at from 100 to 120° C.

A further modification which can be carried out on aluminum-comprising hydroamination catalysts is dealumination, in which part of the aluminum atoms is replaced by silicon or the aluminum content of the hydroamination catalysts is decreased by, for example, hydrothermal treatment. A hydrothermal dealumination is advantageously followed by an extraction with acids or complexing agents in order to remove nonlattice aluminum formed. The replacement of aluminum by silicon can be effected, for example, by means of $(NH_4)_2SiF_6$ or $SiCl_4$. Examples of dealuminations of Y-zeolites may be found in Corma et al., Stud. Surf. Sci. Catal. 37 (1987), pages 495 to 503.

The hydroamination catalysts can be used as extrudates having diameters of, for example, from 1 to 4 mm or as pellets having a diameter of, for example, from 3 to 5 mm for the hydroamination of olefins.

After shaping, the extrudates or pressed bodies are advantageously dried at from 80 to 150° C. for from 2 to 16 hours, for example at 110° C./16 hours, and calcined at from 300 to 500° C. for from 2 to 16 hours, with calcination also being able, like the activation, to be carried out directly in the hydroamination reactor.

In a preferred embodiment, calcined hydroamination catalysts are used in the process of the invention.

The reaction of the olefin with ammonia and/or the primary or secondary amine in the presence of the inorganic solid-stage acid can be carried out, for example, as described in EP-A 132 736, EP-A 752 409, EP-A 822 179 and WO-A-02/00597.

The reaction can be carried out continuously, batchwise or in the semibatch mode.

In general, ammonia and/or primary amine or, if appropriate, secondary amine is preferably mixed together with olefin in a molar ratio of from 1:1 to 10:1, preferably from 1:1 to 5:1, particularly preferably from 1:1 to 3:1, and reacted in the gas phase or in the supercritical state at a pressure of from 40 to 700 bar abs., preferably from 200 to 300 bar abs., and a temperature of from 80 to 400° C., preferably from 230 to 320° C., in a fixed-bed or fluidized-bed reactor comprising the hydroamination catalyst which has been pretreated according to the invention.

As an alternative, the reaction can be carried out in the liquid phase at a pressure of from 40 to 80 bar abs. and a temperature of from 60 to 120° C. in a solid-liquid fluidized-bed reactor or a flow tube reactor comprising the hydroamination catalyst which has been pretreated according to the invention.

A particular embodiment of this process comprises feeding ammonia and/or the primary or secondary amine mixed with the olefin or the olefin mixture in a molar ratio of from 1:1 to 5:1, preferably from 1:1 to 3:1, into a fixed-bed reactor comprising the hydroamination catalyst which has been pretreated according to the invention and reacting the mixture in the gas phase or in the supercritical state at a pressure of from 100 to 320 bar abs., preferably from 150 to 310 bar abs., in particular from 200 to 300 bar abs., and a temperature of from 200 to 350° C., preferably from 220 to 330° C., in particular from 230 to 320° C.

The position of the equilibrium and thus the conversion to the desired hydroamination product is greatly dependent on the reaction pressure chosen. A higher pressure favors the addition product, but the pressure range up to 300 bar abs. generally represents the optimum for technical and economic reasons. The selectivity of the reaction is influenced to a great extent by the temperature and also parameters such as ammonia/amine excess and catalyst. Although the reaction rate of the addition reaction increases greatly with increasing temperature, selectivity-reducing secondary reactions may be promoted at the same time. In addition, an increase in temperature is usually not advantageous from a thermodynamic point of view. The position of the temperature optimum with regard to conversion and selectivity is dependent on the constitution of the olefin, of the primary amine used and of the catalyst and is usually in the range from 220 to 320° C.

After the reaction, the product of the hydroamination reaction is usually separated off, e.g. by distillation, rectification, filtration, scrubbing with water or adsorption.

Unreacted starting materials or inert gases introduced can be recirculated to the reaction.

In the process of the invention, ammonia, primary or secondary amines are used. The primary or secondary amines preferably have $C_{1-20}$-alkyl radicals, particularly preferably $C_{1-6}$-alkyl radicals, in particular methyl radicals or ethyl radicals.

As olefins, preference is given to using $C_{2-20}$-olefins which are aliphatic. They can be linear or branched. Preference is given to using $C_{2-12}$-olefins, in particular $C_{2-6}$-olefins. Examples of suitable olefins are ethene, propene, butene, isobutene and also 1,3-butadiene. In a particularly preferred embodiment, isobutene is used as olefin.

Apart from ammonia, very particularly preferred amines are monomethylamine, dimethylamine, monoethylamine, diethylamine, n-butylamine, isopropylamine, diisopropylamine and di-n-butylamine. In a particularly preferred embodiment, ammonia is used.

Hydroamination products from ethene and ammonia are monoethylamine, diethylamine and/or triethylamine, from ethene and monoethylamine: diethylamine and/or triethylamine, from isobutene and ammonia, tert-butylamine, from 1,3-butadiene and ammonia: 1-amino-3-butene and/or 2-amino-3-butene, from 1,3-butadiene and n-butylamine: (2-butenyl)-n-butylamine and/or (3-butenyl)-n-butylamine and from propene and isopropylamine, diisopropylamine.

In a particularly preferred embodiment, the hydroamination product is tert-butylamine produced from isobutene and ammonia.

The tert-butylamine prepared according to the invention can be used as raw material in the rubber industry (vulcanization accelerator) or for the preparation of crop protection agents or pharmaceuticals.

Thermal damage to the hydroamination catalysts on starting up the catalyst is generally reduced by the process of the invention for the pretreatment of hydroamination catalysts. Thus, a hydroamination process which displays long periods of operation and makes it possible to obtain hydroamination product in a high yield and selectivity is made available. The operating life of the catalyst before regeneration may be required is increased by the process of the invention. A further object of the present invention was to develop a process for starting up a hydroamination catalyst, which leads to reduced thermal damage to the catalysts used, so that the activity of the catalysts is retained for a long time.

The invention is illustrated by the following examples.

COMPARATIVE EXAMPLE 1

In an adiabatic calorimeter, a hydroamination catalyst comprising type SSZ-26 zeolite is supplied with ammonia and isobutene. The temperature at the beginning of the reaction (start temperature) is 22° C. The temperature rise after introduction of the starting materials is measured. The temperature in the calorimeter rises to a maximum temperature of 75° C. The precise experimental parameters are shown in Table 1.

EXAMPLE 1

In an adiabatic calorimeter, a hydroamination catalyst comprising type SSZ-26 zeolite is, according to the invention, firstly supplied with ammonia. This results in a temperature rise from 21° C. (start temperature) to 42° C. After depressurization and therefore removal of the ammonia from the calorimeter, the catalyst is brought back to the start temperature and supplied with ammonia and isobutene. The temperature rise after introduction of the starting material is measured. The temperature in the calorimeter rises to a maximum temperature of 24° C. The precise experimental parameters are shown in Table 2.

TABLE 1

| | Comparative example | Example 1 |
|---|---|---|
| Volume of reaction vessel | 114 ml | 114 ml |
| Amount of catalyst | 33.22 g | 33.83 g |
| Amount of $NH_3$ for pretreatment | 0 g | 31.90 g |
| Amount of $NH_3$/isobutene mixture | 29.17 g | 32.47 g |
| Isobutene content of the $NH_3$/isobutene mixture | 69.8% by weight | 68.4% by weight |
| Start temperature | 22° C. | 21° C. |
| Temperature after introduction of $NH_3$/isobutene mixture | 75° C. | 24° C. |

On an industrial scale, the heat involved on starting up or supplying the catalyst with starting materials is difficult to remove, so that the resulting temperature rise leads to thermal damage to the catalyst. The experiment according to the invention is able to show that the pretreatment according to the invention of the hydroamination catalysts is able to reduce the quantity of heat evolved on starting up catalysts significantly, so that thermal damage to the hydroamination catalyst is largely avoided.

COMPARATIVE EXAMPLE 2

In an adiabatic calorimeter, a hydroamination catalyst comprising type NU-85 zeolite is supplied with ammonia and isobutene. The temperature at the beginning of the reaction (start temperature) is 22° C. The temperature rise after introduction of the starting materials is measured. The temperature in the calorimeter rises to a maximum temperature of 70° C. The precise experimental parameters are shown in Table 1.

EXAMPLE 2

In an adiabatic calorimeter, a hydroamination catalyst comprising type NU-85 zeolite is, according to the invention, firstly supplied with ammonia. This results in a temperature rise from 21° C. (start temperature) to 44° C. After depressurization and therefore removal of the ammonia from the calorimeter, the catalyst is brought back to the start temperature and supplied with ammonia and isobutene. The temperature rise after introduction of the starting materials is measured. The temperature in the calorimeter rises to a maximum temperature of 25° C. The precise experimental parameters are shown in Table 2.

TABLE 2

| | Comparative example | Example 2 |
|---|---|---|
| Volume of reaction vessel | 114 ml | 114 ml |
| Amount of catalyst | 33.44 g | 33.25 g |
| Amount of NH$_3$ for pretreatment | 0 g | 32.05 g |
| Amount of NH$_3$/isobutene mixture | 30.14 g | 32.37 g |
| Isobutene content of the NH$_3$/isobutene mixture | 69.8% by weight | 68.4% by weight |
| Start temperature | 22° C. | 21° C. |
| Temperature after introduction of NH$_3$/isobutene mixture | 70° C. | 25° C. |

COMPARATIVE EXAMPLE 3

In an adiabatic calorimeter, a hydroamination catalyst comprising type MCM-49 zeolite is supplied with ammonia and isobutene. The temperature at the beginning of the reaction (start temperature) is 22° C. The temperature rise after introduction of the starting materials is measured. The temperature in the calorimeter rises to a maximum temperature of 72° C. The precise experimental parameters are shown in Table 1.

EXAMPLE 3

In an adiabatic calorimeter, a hydroamination catalyst comprising type MCM-49 zeolite is, according to the invention, firstly supplied with ammonia. This results in a temperature rise from 21° C. (start temperature) to 43° C. After depressurization and therefore removal of the ammonia from the calorimeter, the catalyst is brought back to the start temperature and supplied with ammonia and isobutene. The temperature rise after introduction of the starting materials is measured. The temperature in the calorimeter rises to a maximum temperature of 26° C. The precise experimental parameters are shown in Table 2.

TABLE 3

| | Comparative example | Example 3 |
|---|---|---|
| Volume of reaction vessel | 114 ml | 114 ml |
| Amount of catalyst | 33.75 g | 34.05 g |
| Amount of NH$_3$ for pretreatment | 0 g | 31.75 g |
| Amount of NH$_3$/isobutene mixture | 31.82 g | 32.57 g |
| Isobutene content of the NH$_3$/isobutene mixture | 69.8% by weight | 68.4% by weight |
| Start temperature | 22° C. | 21° C. |
| Temperature after introduction of NH$_3$/isobutene mixture | 72° C. | 26° C. |

COMPARATIVE EXAMPLE 4 in an adiabatic calorimeter, a hydroamination catalyst comprising type boron-BETA-zeolite in a γ-Al$_2$O$_3$ matrix (zeolite content: 75% by weight) is supplied with ammonia and isobutene. The temperature at the beginning of the reaction (start temperature) is 22° C. The temperature rise after introduction of the starting materials is measured. The temperature in the calorimeter rises to a maximum temperature of 73° C. The precise experimental parameters are shown in Table 1.

EXAMPLE 4

In an adiabatic calorimeter, a hydroamination catalyst comprising type boron-BETA-zeolite in a γ-Al$_2$O$_3$ matrix (zeolite content: 75% by weight) is, according to the invention, firstly supplied with ammonia. This results in a temperature rise from 21° C. (start temperature) to 44° C. After depressurization and therefore removal of the ammonia from the calorimeter, the catalyst is brought back to the start temperature and supplied with ammonia and isobutene. The temperature rise after introduction of the starting materials is measured. The temperature in the calorimeter rises to a maximum temperature of 26° C. The precise experimental parameters are shown in Table 1.

TABLE 4

| | Comparative example | Example 4 |
|---|---|---|
| Volume of reaction vessel | 114 ml | 114 ml |
| Amount of catalyst | 33.53 g | 33.62 g |
| Amount of NH$_3$ for pretreatment | 0 g | 31.90 g |
| Amount of NH$_3$/isobutene mixture | 30.78 g | 31.95 g |
| Isobutene content of the NH$_3$/isobutene mixture | 69.8% by weight | 68.4% by weight |
| Start temperature | 22° C. | 21° C. |
| Temperature after introduction of NH$_3$/isobutene mixture | 73° C. | 26° C. |

COMPARATIVE EXAMPLE 5

In an adiabatic calorimeter, a hydroamination catalyst comprising type boron-MCM-22 zeolite is supplied with ammonia and isobutene. The temperature at the beginning of the reaction (start temperature) is 21° C. The temperature rise after introduction of the starting materials is measured. The temperature in the calorimeter rises to a maximum temperature of 78° C. The precise experimental parameters are shown in Table 1.

EXAMPLE 5

In an adiabatic calorimeter, a hydroamination catalyst comprising type boron-MCM-22 zeolite is, according to the invention, firstly supplied with ammonia. This results in a temperature rise from 22° C. (start temperature) to 44° C. After depressurization and therefore removal of the ammonia from the calorimeter, the catalyst is brought back to the start temperature and supplied with ammonia and isobutene. The temperature rise after introduction of the starting materials is measured. The temperature in the calorimeter rises to a maximum temperature of 25° C. The precise experimental parameters are shown in Table 2.

TABLE 5

|  | Comparative example | Example 5 |
|---|---|---|
| Volume of reaction vessel | 114 ml | 114 ml |
| Amount of catalyst | 33.31 g | 33.72 g |
| Amount of $NH_3$ for pretreatment | 0 g | 31.90 g |
| Amount of $NH_3$/isobutene mixture | 31.15 g | 32.42 g |
| Isobutene content of the $NH_3$/isobutene mixture | 69.8% by weight | 68.4% by weight |
| Start temperature | 21° C. | 21° C. |
| Temperature after introduction of $NH_3$/isobutene mixture | 78° C. | 25° C. |

COMPARATIVE EXAMPLE 6

In an adiabatic calorimeter, a hydroamination catalyst comprising type NES zeolite is supplied with ammonia and isobutene. The temperature at the beginning of the reaction (start temperature) is 22° C. The temperature rise after introduction of the starting materials is measured. The temperature in the calorimeter rises to a maximum temperature of 72° C. The precise experimental parameters are shown in Table 1.

EXAMPLE 6

In an adiabatic calorimeter, a hydroamination catalyst comprising type NES zeolite is, according to the invention, firstly supplied with ammonia. This results in a temperature rise from 22° C. (start temperature) to 42° C. After depressurization and therefore removal of the ammonia from the calorimeter, the catalyst is brought back to the start temperature and supplied with ammonia and isobutene. The temperature rise after introduction of the starting materials is measured. The temperature in the calorimeter rises to a maximum temperature of 24° C. The precise experimental parameters are shown in Table 2.

TABLE 6

|  | Comparative example | Example 6 |
|---|---|---|
| Volume of reaction vessel | 114 ml | 114 ml |
| Amount of catalyst | 33.00 g | 33.98 g |
| Amount of $NH_3$ for pretreatment | 0 g | 31.90 g |
| Amount of $NH_3$/isobutene mixture | 29.96 g | 29.90 g |
| Isobutene content of the $NH_3$/isobutene mixture | 69.8% by weight | 68.4% by weight |
| Start temperature | 22° C. | 21° C. |
| Temperature after introduction of $NH_3$/isobutene mixture | 72° C. | 24° C. |

The invention claimed is:

1. A process for the pretreatment of hydroamination catalysts comprising:
    contacting a hydroamination catalyst with an ammonia-comprising mixture at a temperature of from 0 to 50° C., the ammonia-comprising mixture comprising greater than 55% by weight of ammonia, less than 40% by weight of olefin and less than 5% by weight of further constituents,
    wherein the contacting step occurs before reacting olefins with ammonia, a primary or secondary amine over the hydroamination catalyst.
2. The process of claim 1, wherein the ammonia-comprising mixture comprises less than 10% by weight of olefin.
3. The process of claim 1, wherein the ammonia-comprising mixture is brought into contact with the hydroamination catalyst together with one or more inert gases.
4. The process of claim 1, wherein contacting step is performed at a pressure of from 0.1 to 50 bar abs.
5. The process of claim 1, wherein the hydroamination catalyst has not previously been used in a hydroamination reaction.
6. The process of claim 1, wherein the hydroamination catalyst is a regenerated hydroamination catalyst.
7. The process of claim 1, wherein the hydroamination catalyst is a thermally activated hydroamination catalyst.
8. The process of claim 1, wherein the hydroamination catalyst is a calcined zeolytic hydroamination catalyst.
9. The process of claim 1, wherein the pretreatment process is carried out in a continuously operated reactor.
10. The process of claim 1, wherein the pretreatment process is carried out in an adiabatically operated reactor.
11. A process for preparing alkylamines comprising:
    reacting olefins with ammonia, primary or secondary amines over a hydroamination catalyst,
    wherein the hydroamination catalyst is pretreated in accordance with claim 1 before reacting step.
12. The process of claim 11, wherein a molar ratio of the ammonia, primary or secondary amines to the olefins is in the range from 1:1 to 3:1.
13. The process of claim 11, wherein the olefins are reacted with ammonia.
14. The process of claim 11, wherein the olefins comprise an isobutene.
15. A process for the pretreatment of hydroamination catalysts comprising:
    contacting a hydroamination catalyst with an ammonia-comprising mixture at a temperature of from 0 to 50° C., the ammonia-comprising mixture comprising greater than 55% by weight of ammonia, less than 40% by weight of olefin and less than 5% by weight of further constituents,
    wherein the pretreated catalyst is effective to limit the increase of a temperature of an adiabatic environment to about 5° C. after introducing the pretreated catalyst and a mixture of ammonia and an olefin into the adiabatic environment, and
    wherein the ratio of the volume of the adiabatic environment in milliliters to the mass of the mixture of ammonia and an olefin in grams is less than 4:1.
16. The process of claim 15, wherein the hydroamination catalyst comprises a zeolite selected from the group consisting of an SSZ-26 type zeolite, an NU-85 type zeolite, an MCM-49 type zeolite, a boron-BETA type zeolite in a gamma-Al2O3 matrix, a boron-MCM-22 type zeolite, and an NES-type zeolite and the olefin is isobutene.

* * * * *